US012558080B2

(12) United States Patent
Calvo et al.

(10) Patent No.: US 12,558,080 B2
(45) Date of Patent: Feb. 24, 2026

(54) DEVICES, SYSTEMS, AND METHODS FOR TISSUE TRACTION

(71) Applicant: BOSTON SCIENTIFIC SCIMED, INC., Maple Grove, MA (US)

(72) Inventors: Yeison Calvo, San Ramón (CR); Barry Weitzner, Acton, MA (US); Jimena Cespedes Berrocal, Alajuela (CR); Juan Pablo Ortiz Garcia, San Isidro (CR); Rosa Angelica Perez Chaves, Heredia (CR); Christian Araya Camacho, Alajuela (CR); Julián Fuentes Castro, Cartago (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 397 days.

(21) Appl. No.: 18/107,291

(22) Filed: Feb. 8, 2023

(65) Prior Publication Data

US 2023/0248346 A1 Aug. 10, 2023

Related U.S. Application Data

(60) Provisional application No. 63/308,245, filed on Feb. 9, 2022.

(51) Int. Cl.
*A61B 17/02* (2006.01)
*A61B 17/00* (2006.01)

(52) U.S. Cl.
CPC .. *A61B 17/0218* (2013.01); *A61B 2017/0034* (2013.01); *A61B 2017/00862* (2013.01); *A61B 2017/0225* (2013.01)

(58) Field of Classification Search
CPC .............. A61B 17/0218; A61B 17/083; A61B 2017/00269; A61B 17/088; A61B 2017/0225; A61B 17/0281

(Continued)

(56) References Cited

U.S. PATENT DOCUMENTS 5,582,577 A * 12/1996 Lund ................... A61B 17/0218
600/233
2008/0234551 A1 9/2008 Lin et al.
(Continued)

FOREIGN PATENT DOCUMENTS

DE 212019000166 U1 8/2020
JP 2008142516 A 6/2008

OTHER PUBLICATIONS

International Search Report and Written Opinion dated Apr. 28, 2023 International Application No. PCT/US2023/012616.

*Primary Examiner* — Eduardo C Robert
*Assistant Examiner* — Tara Rose E Carter
(74) *Attorney, Agent, or Firm* — Seager, Tufte & Wickhem, LLP

(57) ABSTRACT

A tissue traction device having a target-tissue-engaging segment and more than one traction-tissue-engaging segment spaced apart from the target-tissue-engaging segment. The tissue traction device may have a peripheral section with at least one traction-tissue-engagement section therein, with at least one of the traction-tissue-engaging segments defined on such traction-tissue-engagement section. An additional traction-tissue-engagement segment may be defined within the peripheral section, optionally on an additional traction-tissue-engagement section, and/or within the at least one traction-tissue-engagement section. One or more traction-tissue-engagement segments within the peripheral section may be simultaneously and/or sequentially engaged with traction tissue to achieve varying force vectors of traction on the target tissue. A hanger may be provided on a tissue-engagement member or on the peripheral section of the tissue traction device to hold one or more of the traction-tissue-engaging segments extended from (Continued)

within the peripheral section of the tissue traction device to the traction tissue.

20 Claims, 4 Drawing Sheets

(58) Field of Classification Search
USPC ................................................. 600/201–245
See application file for complete search history.

(56) References Cited

U.S. PATENT DOCUMENTS

2020/0360006 A1 * 11/2020 Sluti ................... A61B 17/0293
2020/0390446 A1 * 12/2020 Weitzner ............ A61B 17/1285
2021/0169464 A1    6/2021 Lee et al.

* cited by examiner

DEVICES, SYSTEMS, AND METHODS FOR TISSUE TRACTION

CROSS-REFERENCE TO RELATED APPLICATIONS

This application claims the benefit of priority of U.S. Provisional Application No. 63/308,245, filed Feb. 9, 2022, the entire disclosure of which is hereby incorporated by reference herein for all purposes.

FIELD

The present disclosure relates generally to the field of implantable medical devices. In particular, the present disclosure relates to medical devices, systems, and methods for cardiac treatment.

BACKGROUND

Various surgical procedures involves lifting or separating target tissue (a designated section of tissue) at a treatment site, such as while the target tissue is still attached to the treatment site. A tissue traction element may be used to lift the target tissue away from the treatment site at which the procedure is being performed. In some instances, the target tissue is an unhealthy, diseased (i.e., cancerous, pre-cancerous etc.), or otherwise undesirable portion of tissue that may be healthy or unhealthy. A "target tissue" may also include tissues that are suspected of being unhealthy or diseased, but which require surgical removal for verification of their disease status by biopsy. Endoscopic Submucosal Dissection (ESD) and Endoscopic Mucosal Resection (EMR) are examples of outpatient procedures for removing deep tumors from the gastrointestinal (GI) tract. Even though this technique can allow patients to recover faster and often with less pain than with open or laparoscopic surgical procedures, such techniques require a high degree of expertise, and therefore are not yet widely adopted. One of the largest time and complexity drivers is managing the tissue being dissected/resected. As the medical professional cuts the tissue, it becomes harder to visualize the cutting plane (tissue to be cut) as tissue remains above the cutting plane, and also because the medical professional needs to cut continually deeper into the tissue. Accurately and efficiently performing an endoscopic tissue resection/dissection procedure includes the ability to maintain traction on the target tissue above the cutting plane as the boundaries of the target tissue are dissected and the tissue under traction is being lifted. Traction systems may be unable to maintain or adjust tension applied to the target tissue, possibly obstructing a medical professional's view of the target tissue and/or interfering with accessory tools. These complications may directly contribute to increased procedures time, complexity, and risk of perforation or bleeding. Accordingly, improvements to tissue traction devices, systems, and methods would be welcome in the medical profession.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a tissue traction system includes a tissue traction device defining a target-tissue-engaging segment engageable with target tissue; a tissue-engagement member configured to engage at least one traction-tissue-engaging segment with the traction tissue; and a hanger configured to hold at least one traction-tissue-engaging segment adjacent the traction tissue.

In some embodiments, the tissue traction device includes a peripheral section defining a perimeter, and the at least one traction-tissue-engaging segment is provided within the perimeter of the peripheral section of the tissue traction device. In some embodiments, the target-tissue-engaging segment is defined along the peripheral section. In some embodiments, the peripheral section is in the form of a loop; and the at least one traction-tissue-engaging segment within the peripheral section is defined on a loop-shaped traction-tissue-engaging section within the peripheral section. In some embodiments, the target-tissue-engaging segment is defined along the peripheral section; and the loop-shaped traction-tissue-engaging section within the peripheral section is internally tangent with the peripheral section adjacent the target-tissue-engaging segment. In some embodiments, the tissue traction system includes an additional traction-tissue-engaging segment within the peripheral section. In some embodiments, the additional traction-tissue-engaging segment is defined on an additional loop-shaped traction-tissue-engaging section within the peripheral section. In some embodiments, the target-tissue-engaging segment is defined along the peripheral section; the additional loop-shaped traction-tissue-engaging section is within the loop-shaped traction-tissue-engaging section; and the peripheral section, the loop-shaped traction-tissue-engaging section, and the additional loop-shaped traction-tissue-engaging section are internally tangent adjacent the target-tissue-engaging segment.

In some embodiments, the hanger is on the tissue-engagement member.

In some embodiments, the hanger is on the tissue traction device.

In accordance with various principles of the present disclosure, a tissue traction device includes a peripheral section defining a perimeter of the tissue traction device; and a first traction-tissue-engaging section extending within the perimeter of and coupled to the peripheral section.

In some embodiments, the peripheral section defines a target-tissue-engaging segment engageable with target tissue; and the first traction-tissue-engaging section defines at least one traction-tissue-engaging segment spaced apart from the target-tissue-engaging segment and engageable with traction tissue. In some embodiments, the peripheral section and the first traction-tissue-engaging section are each in the form of a loop; and the first traction-tissue-engaging section is internally tangent with the peripheral section adjacent the target-tissue-engaging segment.

In some embodiments, the tissue traction device includes a second traction-tissue-engaging section within the peripheral section. In some embodiments, the second traction-tissue-engaging section is within the first traction-tissue-engaging section. In some embodiments, the peripheral section defines a target-tissue-engaging segment engageable with target tissue; the peripheral section, the first traction-tissue-engaging section, and the second traction-tissue-engaging section are each in the form of a loop; and the first traction-tissue-engaging section and the second traction-tissue-engaging section are internally tangent with the peripheral section adjacent the target-tissue-engaging segment.

In some embodiments, the peripheral section defines a target-tissue-engaging segment engageable with target tissue and a traction-tissue-engaging segment spaced apart from the target-tissue-engaging segment and engageable with traction tissue; and the tissue traction device further may include a hanger on the peripheral section adjacent the traction-tissue-engaging segment configured to hold a traction-tissue-engaging segment of the first traction-tissue-engaging section adjacent the traction tissue.

In accordance with various principles of the present disclosure a tissue-engagement member includes grasper arms engageable with tissue; and a hanger spaced apart from the grasper arms and configured to hold at least one traction-tissue-engaging segment of a tissue traction device adjacent the tissue.

In some embodiments, the tissue-engagement member includes a capsule extending about the grasper arms, where the grasper arms are retractable into the capsule to shift into a closed configuration holding tissue therebetween, and the hanger extends from the capsule.

In some embodiments, the grasper arms are further engageable with another traction-tissue-engaging segment of the tissue traction device to engage the other traction-tissue-engaging segment of the tissue traction device with tissue.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figures 1, 2:
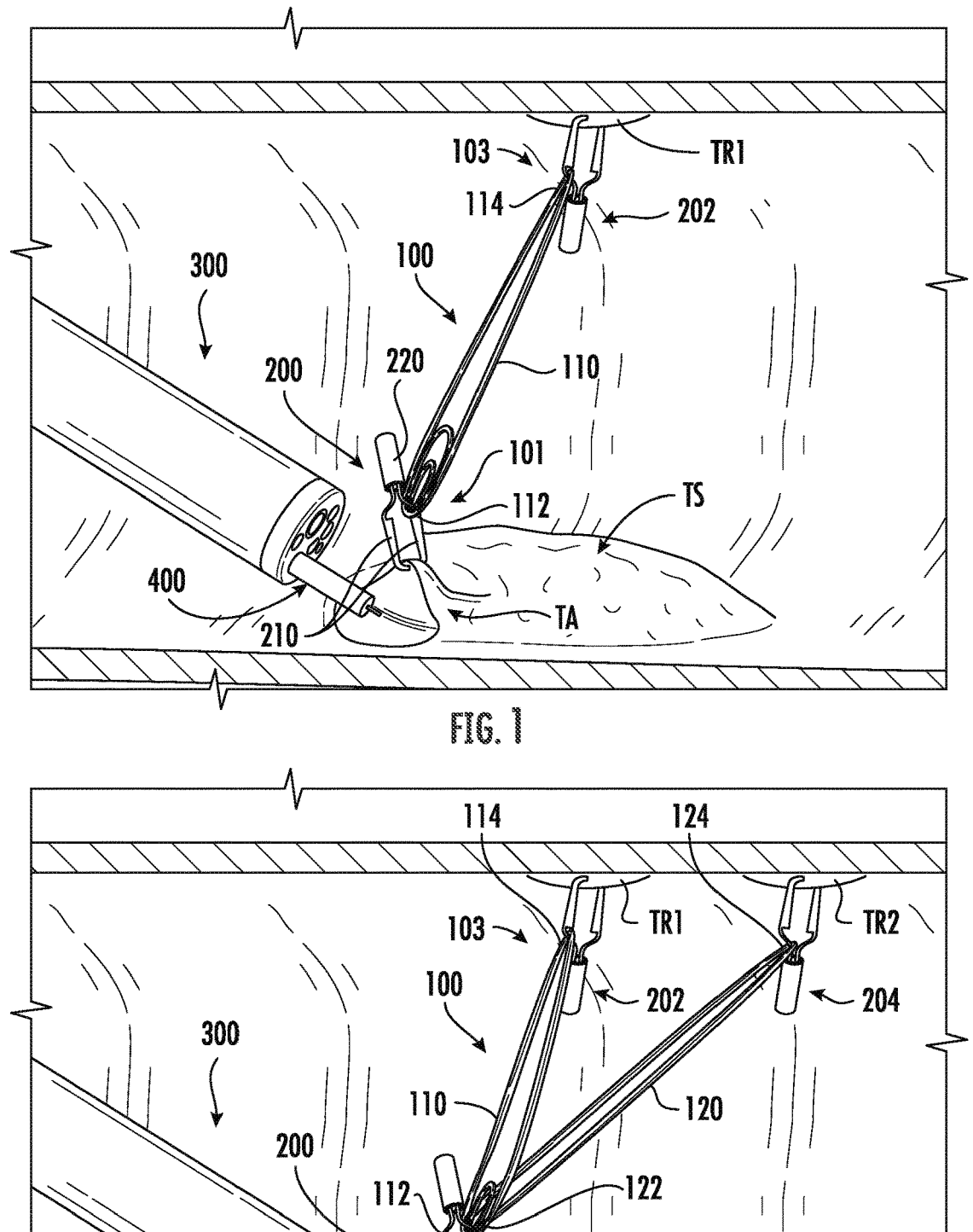
FIG. 1 illustrates an example of an environment in which devices, systems, and methods in accordance with various principles of the present disclosure may be used with an example of an embodiment of a traction device and system being implemented.
FIG. 2 illustrates an example of an environment as in FIG. 1 with an example of an embodiment of a traction device and system as in FIG. 1 being further implemented.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and/or closest to a delivery device, and "distal" refers to the direction or location furthest from the user, such as when using the device (e.g., introducing the device into a patient, or during implantation, positioning, or delivery), and/or closest to a delivery device. "Longitudinal" means extending along the longer or larger dimension of an element. "Central" means at least generally bisecting a center point and/or generally equidistant from a periphery or boundary, and a "central axis" means, with respect to an opening, a line that at least generally bisects a center point of the opening, extending longitudinally along the length of the opening when the opening comprises, for example, a tubular element, a channel, a cavity, or a bore. As used herein, a "free end" of an element is a terminal end at which such element does not extend beyond.

The present disclosure relates to a variety of devices, systems, and methods for applying traction to tissue within a body. A number of medical procedures, including those performed along the digestive and/or biliary tract, utilize medical devices to access tissue intended for removal (e.g., "target tissue") within the body. For example, in some current medical procedures (e.g., endoscopic submucosal dissection (ESD), endoscopic mucosal resection (EMR), Peroral Endoscopic Myotomy (POEM), cholecystectomy, Video-Assisted Thoracoscopic Surgery (VATS)), medical professionals may utilize an endoscope or similar medical device during access and removal of diseased lesions. The endoscope may be capable of both accessing the target tissue site (the site at which the target tissue is located) while also permitting various tissue manipulating devices to be deployed therethrough. Such tissue manipulating devices include, without limitation, devices for resecting target tissue, which include, without limitation, cutting devices such as knives, scalpels, scissors, electrocauterization devices, end effectors, graspers, snares, forceps, dissectors, energy-based tissue coagulators or cutters, clamps, tissue staplers, tissue loops, clip appliers, suture delivering instruments, etc., the particular device not being critical to the present disclosure. It will be appreciated that terms such as medical tools, instruments, devices, etc., may be used interchangeably herein without intent to limit. Additionally, in some instances, an endoscope may incorporate features which assist the medical professional in visualizing and/or imaging the tissue dissection/resection procedure, such as to facilitate performance of the procedure. For example, some endoscopes may include a light and/or camera designed to illuminate and/or visualize the treatment site/target tissue area as the endoscope is navigated and positioned adjacent to the target tissue site. Additionally, some endoscopes may also include a lumen (e.g., a working channel) through which a further instrument, and optionally also a delivery sheath for the instrument, may be deployed and utilized. Additional visualization methods (e.g., fluoroscopy) may be alternatively or additionally employed. It will be appreciated that reference is made herein to tissue resection (and other grammatical forms thereof) for the sake of convenience, such term encompassing tissue dissection, cutting, manipulation, etc. (and other grammatical forms thereof) without intent to limit.

While physicians are becoming more proficient at resecting diseased lesions from within the body (e.g., within the digestive tract, abdominal cavity, thoracic cavity, etc.), present traction methods may continue to be inefficient to the physician. For example, in some instances poor visualization and poor ability to engage and manipulate tissue may result in a prolonged tissue dissection procedure. It may be desirable to lift or to retract the tissue out of the field of vision or out of the way of the instrument being used to perform the procedure. For instance, in some EMR/ESD procedures, physicians may use separate devices to provide a means of tissue traction, such as to move tissue with respect to surrounding tissue. Positioning and maneuvering (e.g., traction) of a resected tissue flap during and after resecting presents various challenges. Such procedures may include multiple device manipulations and/or exchanges, and accompanying extended procedure times. Such systems may be unable to maintain or adjust traction or tension applied to the target tissue, and/or may maintain or adjust traction or tension applied to the target tissue in an inefficient or inconsistent manner.

In accordance with various principles of the present disclosure, a tissue traction device is used to apply traction to tissue to facilitate performance of a procedure with respect to such tissue. The tissue traction device (which may be alternately referenced herein as a tether for the sake of convenience and without intent to limit) may be a traction band, elastic band, stretchable elongate member, wire, cord, cable, spring, suture, and/or any other suitable member, which optionally is stretchable and/or elongatable. It will be appreciated that the tether may advantageously be elastic and/or elastomeric (e.g., formed of rubber), though elasticity and/or stretchability are not necessarily aspects of a traction device formed in accordance with various principles of the present disclosure.

The tissue traction device may be engaged with tissue at a target tissue site with a tissue-engagement member, which may alternately be referenced herein as a tissue fastener or clip or other mechanical securing device (e.g., a hemostatic clip, clamp, grasper, basket, gripper, magnet, adhesive, etc.), without intent to limit. It will be appreciated that reference to "at" the target tissue site is intended to include tissue at and about the vicinity of the target tissue, and is not limited to just target tissue. It will be appreciated that terms such as engage (and other grammatical forms thereof) may be used interchangeably herein with terms such as couple, grasp, hold, clasp, clip, anchor, attach, affix, secure, etc. (and other grammatical forms thereof), without intent to limit. The tissue-engagement member is optionally separately formed from the tissue traction device. In some embodiments, the tissue-engagement member is repositionable after being partially deployed. For example, the tissue-engagement member may be configured to allow for the tissue-engagement member to be releasably engaged (e.g., closed, but not locked, into engagement) with tissue when in a first configuration, and locked against opening out of engagement with tissue when in a second closed configuration. In some embodiments, the tissue-engagement member has grasper arms or jaws selectively movable away from each other to engage tissue therebetween, and movable towards each other to grasp the engaged tissue. The grasper arms may be hinged together (e.g., as a single piece), or separately formed and movable with respect to each other, such as by being pivotable about a pivot point. The grasper arms may have one or more additional grasping feature, such as a sawtooth or crenulated profile or teeth, at ends and/or along edges of the grasper arms. In some embodiments, the tissue-engagement member is movable with respect to the tissue traction device, even when coupled thereto. Movement, such as rotation (e.g., 360° rotation), of the tissue-engagement member may be controlled by a proximal control knob, dongle, or other actuator element. In some embodiments, the tissue-engagement member may be maneuvered, e.g., rotated, with one-to-one correspondence between movement of a control knob and the tissue-engagement member. In some embodiments, the tissue-engagement member is releasable from the delivery device used to deliver the tissue-engagement member. For instance, a frangible connection between the tissue-engagement member and the delivery device may be overcome and/or a threshold pressure may be exerted to separate a jointed (e.g., ball and yoke) connection. It will be appreciated that the present disclosure is not to be limited to a particular form or configuration of a tissue-engagement member. In some embodiments, the tissue traction device is delivered to the target tissue site with a tissue-engagement member coupled thereto.

In accordance with various principles of the present disclosure, a tissue traction device has a target-tissue-engaging section or segment configured and positioned to be engaged with tissue at the target tissue site. Such engagement of the target-tissue-engaging segment with tissue may be direct or indirect, such as with the use of an initial or first tissue-engagement member (optionally pre-loaded or otherwise coupled to the tissue traction device prior to delivery to the target tissue site). For the sake of convenience, and without intent to limit, the tissue which is initially engaged by the tissue traction device is referenced herein as the target tissue, although tissue other than the target tissue may be initially engaged instead. Another section of the tissue traction device (referenced herein as an initial or first traction-tissue-engaging section) is then engaged with tissue spaced apart from the target tissue (referenced herein as a first traction tissue site without intent to limit), such as in a manner which allows the tissue traction device to apply traction to the target tissue. A second tissue-engagement member may be used to engage the traction-tissue-engaging section of the tissue traction device with the traction tissue site. As the target tissue is moved with respect to the surrounding tissue (e.g., cut with respect to surrounding tissue), the traction applied thereto by the tissue traction device may decrease. In accordance with various principles of the present disclosure, rather than moving the traction-tissue-engaging section of the tissue traction device to another location to increase tension on the target tissue, one or more additional traction-tissue-engaging sections of the tissue traction device may be engaged with traction tissue to increase the traction applied to the target tissue site. It will be appreciated that the additional traction-tissue-engaging sections of the tissue traction device may be engaged at essentially at the same traction tissue site (depending on the size, shape, configuration, and/or location of the various traction-tissue-engagement sections) or at different traction tissue sites (such as increasingly further from the target tissue). For instance, if the distance between the target tissue and the various traction-tissue-engaging sections of the tissue traction device are different, different force vectors of traction may be applied by the different traction-tissue-engaging segments even if engaged at a common traction tissue site.

In accordance with various principles of the present disclosure, a tissue traction device is shaped to allow different points of attachment of the tissue traction device to tissue, such as with the use of a tissue-engagement member. For instance, in some embodiments, a tissue traction device formed in accordance with various principles of the present disclosure has more than one grasping section or segment distinct from another grasping section or segment. It will be appreciated that terms such as section or segment or area or portion or the like may be used interchangeably herein without intent to limit, reference being made to a grasping segment of a tissue traction device as a section distinct from another section of the tissue traction device. The different sections of the tissue traction device may be distinguished from one another into different grasping segments defined along a section of the tissue traction device such as by a difference in shape or orientation with respect to another grasping segment of the tissue traction device (such as, without limitation, adjacent or adjoining the grasping segments).

In one aspect, a tissue traction device may be formed in accordance with various principles of the present disclosure with an outer or peripheral section defining one or more grasping segments therealong, and one or more grasping segments defined within the perimeter of the peripheral section. A grasping segment defined along the peripheral section of the tissue traction device or within the peripheral section may be engaged with target tissue to which traction is to be applied, and may be referenced herein as a target-tissue-engaging segment. One or more of the grasping segments defined along the peripheral section of the tissue traction device or within the peripheral section may be engaged with traction tissue spaced apart from the target tissue to apply traction to the target tissue. Such segments may be referenced herein as traction-tissue-engaging segments. In accordance with various principles of the present disclosure, traction-tissue engaging sections may be at progressively further distances from the traction tissue, and/or may be at progressively shorter distances from the target tissue so that engagement of different ones of such traction-tissue-engaging segments to substantially the same traction tissue site alters the force vector of traction applied by the tissue traction device. A tissue traction device formed in accordance with various principles of the present disclosure thus provides a plurality of grasping segments or holding places for the medical professional to grasp to maneuver the tissue traction device and/or to engage the tissue traction device with a selected region of tissue spaced apart from target tissue to vary the force vector of traction applied to the target tissue, thereby improving the usability of the tissue traction device.

In some embodiments, a tissue traction device has a peripheral section in the form of a loop. In some embodiments, one or more additional sections, such as in the form of additional loops, are formed within the peripheral section. For instance, in some embodiments, each additional loop is positioned within another loop. In other words, the loops are nested one within the other. In some embodiments, the nested loops generally are connected with one another so that the loops all together form a tissue traction device as a whole (a unitary element in a single piece rather than as separate loops). In some embodiments, the loops are internally tangent along a common section of the tissue traction device. For instance, in some embodiments, the connected nested loops are all connected at a common section of the tissue traction device, such as along the target-tissue-engaging segment of the tissue traction device. As such, as each smaller loop within the outermost loop (e.g., the peripheral section of the tissue traction device) is extended to engage traction tissue spaced apart from the target tissue, an increasing amount of traction may be applied to the target tissue. The medical professional can have a sense of the difference in traction force to be applied by comparing the relative sizes of the inner loops being grasped to be engaged with traction tissue. Moreover, if each of the nested loops within the peripheral section of the tissue traction device is coupled to the peripheral section in the general area of the target-tissueengaging segment, then traction applied by engaging one of the nested loops with traction tissue is generally applied more directly to the target tissue then if the nested loop were coupled to another region of the peripheral section, and the force vectors of traction may be varied as desired by the user.

A tissue traction device formed in accordance with various principles of the present disclosure allows the medical professional to vary the force vector applied to the target tissue to apply traction thereto. For instance, engaging a first segment of the tissue traction device to a first region of tissue (such as, without limitation, target tissue), and then engaging (sequentially or at the same time) different segments of the tissue traction device to different regions of tissue spaced apart from the first region of tissue allows varying degrees or intensities and/or varying angles of traction to be applied to the target tissue. If the medical professional engages a target-tissue-engaging segment of the tissue traction device to a target tissue site, and a traction-tissue-engaging segment of the tissue traction device to a traction tissue site, and then needs to adjust the traction on the target tissue site (e.g., to apply additional, greater traction to the target tissue site, or traction at a different angle), an additional traction-tissue-engaging segment of the tissue traction device may be engaged with the traction tissue or at an additional traction tissue site spaced apart from the traction tissue to apply a greater amount of traction to the target tissue and/or traction at a different angle.

In some embodiments, in order to engage more than one traction-tissue-engaging segment of a tissue traction device with substantially the same traction tissue, a tissue-engagement member is configured, in accordance with various principles of the present disclosure, to be engageable with more than one segment of the tissue traction device. In some embodiments, a traction device hanger is formed on a portion of a tissue-engagement member and sized, shaped, configured, and/or dimensioned to receive more than one segment of a tissue traction device formed in accordance with various principles of the present disclosure with multiple traction-tissue-engaging segments.

In some embodiments, a tissue traction device formed in accordance with various principles of the present disclosure (such as with more than one traction-tissue-engaging segment) includes a traction device hanger sized, shaped, configured, and/or dimensioned to receive more than one traction-tissue-engaging segment of the tissue traction device. In such embodiment the size/extent of the tissue traction device is modified by coupling one or more traction-tissue-engaging segments to the hanger to vary traction applied to traction tissue to which the tissue traction device is engaged.

Various embodiments of tissue traction devices, systems, and method of use thereof will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present disclosure is not limited to only the embodiments specifically described herein, and the examples of embodiments disclosed herein are not intended as limiting the broader aspects of the present disclosure.

In the embodiments illustrated in the drawings, it will be appreciated that common features are identified by common reference elements and, for the sake of brevity and convenience, and without intent to limit, the descriptions of the common features are generally not repeated. For purposes of clarity, not all components having the same reference number are numbered. Moreover, certain features in one embodiment may be used across different embodiments and are not necessarily individually labeled when appearing in different embodiments.

Figure 3:
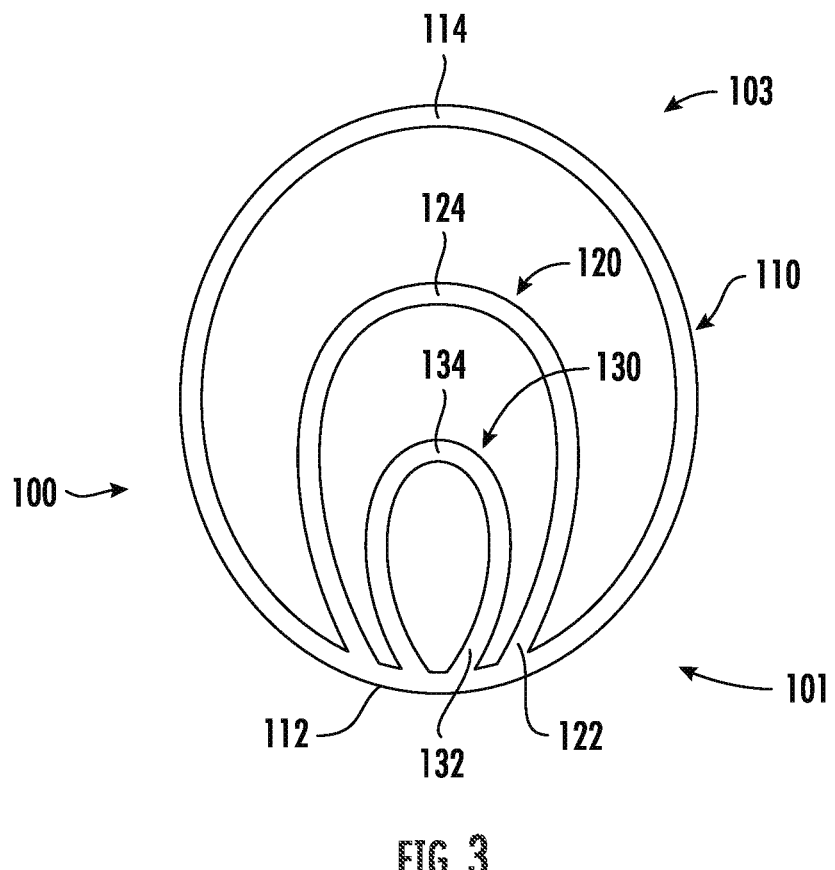
FIG. 3 illustrates a plan view of an example of an embodiment of a traction device formed in accordance with various principles of the present disclosure.

Referring now to FIG. 1 and FIG. 2, an example of a use of a tissue traction device 100 in accordance with various principles of the present disclosure is illustrated. An example of an embodiment of a tissue traction device 100 formed in accordance with various principles of the present disclosure and which may be used as illustrated in FIG. 1 and FIG. 2 is illustrated in FIG. 3. The tissue traction device 100 has a target-tissue-engaging end 101 engaged (directly or indirectly, such as with the use of a tissue-engagement member 200 described in further detail below) with target tissue TA at a target tissue site TS, and a traction-tissue-engaging end 103 engaged (directly or indirectly, such as with the use of a tissue-engagement member 200) with traction tissue TR1 spaced apart from the target tissue TA. Engaged as such, the tissue traction device 100 applies traction to the target tissue TA. It will be appreciated that reference to a first end or a second end of the tissue traction device is for the sake of simplicity, and is not to be understood as being limited to an end of an elongated element, but may also apply to other locations along an element, such as, without limitation, an elongated element.

As may be appreciated with reference to FIG. 3, the illustrated example of an embodiment of a tissue traction device 100 formed in accordance with various principles of the present disclosure has a peripheral section 110 with one or more additional traction sections 120, 130. The peripheral section 110 is generally in the shape of a loop, e.g., a closed shape, such as circle, ellipse, etc., although other shapes are within the scope and spirit of the present disclosure. The peripheral section 110 includes a target-tissue-engaging segment 112 along the target-tissue-engaging end 101 of the tissue traction device 100, and a traction-tissue-engaging segment 114 at a position spaced apart from the target-tissue-engaging segment 112. The target-tissue-engaging segment 112 is engaged with target tissue TA, and the traction-tissue-engaging segment 114 is engaged with traction tissue TR1 in the example of use illustrated in FIG. 1 and FIG. 2. It will be appreciated that other orientations and configurations are within the scope of the present disclosure, the particular locations along the tissue traction device 100 engaged with target tissue TA and traction tissue TR1 not being limited to those illustrated and indicated in the figures. The additional traction sections 120, 130 may be defined with respect to the peripheral section 110 such as within a perimeter defined by the peripheral section 110. As described in further detail below, the additional traction sections 120, 130 may be extended to tissue spaced apart from the target tissue area TA, such as traction tissue TR1 or traction tissue TR2 as illustrated in FIG. 2. As may be appreciated, the additional traction on the target tissue TA causes the target tissue TA to lift further away from the surrounding tissue to allow the procedure being performed on or along the target tissue TA to be continued without interference by the lifted section of the target tissue TA.

In some embodiments, as illustrated in FIG. 1 and FIG. 2, a tissue-engagement member 200 is used to engage the target-tissue-engaging segment 112 with target tissue TA. Alternatively or additionally, a tissue-engagement member 202 is used to engage the traction-tissue-engaging segment 114 of the tissue traction device 100 with traction tissue TR1. In the example of an embodiment illustrated in FIG. 1 and FIG. 2, the tissue-engagement member 200, 202 is an adjustable clip (such as a hemostatic clip) with first and second grasper arms 210 (which may be alternately referenced herein as jaws without intent to limit) movable with respect to each other between an open configuration and a closed configuration. In the open configuration, tissue may be positioned between the grasper arms 210 to be engaged by the grasper arms 210. In the closed configuration, the grasper arms 210 engage or hold tissue therebetween. In some embodiments, the tissue-engagement member 200 includes a capsule 220 into which proximal ends of the grasper arms 210 may be retracted to shift the tissue-engagement member 200 into a closed configuration, and from which the grasper arms 210 may be extended to shift the tissue-engagement member 200 into an open configuration. A controller (not shown, the configuration of which being know to those of ordinary skill in the art and not forming a part of the present disclosure) may be operatively coupled with the grasper arms 210 to actuate movement of the grasper arms 210 (e.g., with respect to the capsule 220) between open and closed configurations. The controller may be separable from the tissue-engagement member 200 once the desired position and/or configuration of the tissue-engagement member 200 has been achieved or reached. The grasper arms 210 may be locked into position with respect to the capsule 220 once the desired location, configuration, etc., of the grasper arms 210 ha been achieved with any of a variety of mechanisms known to those of ordinary skill in the art, the present disclosure not being limited by such structures or features. The tissue-engagement member 200 may be configured to be engaged with tissue as well as a target-tissue-engaging segment 112 and/or traction-tissue-engaging segment 114 of the tissue traction device 100. As such, the target-tissue-engaging segment 112 and/or the traction-tissue-engaging segment 114 of the tissue traction device 100 need not engage tissue directly, but may be engaged with tissue via the tissue-engagement member 200.

An endoscope 300 is illustrated in FIG. 1 and FIG. 2 as delivering a tissue manipulating device 400 to the target tissue site TS to manipulate the target tissue TA to which traction is being applied by the tissue traction device 100. In the illustrated example, the tissue-manipulating device 400 separates the target tissue TA from the surrounding tissue at the target tissue site TS. As the target tissue TA is separated from surrounding tissue, it lifts away, relieving some of the traction exerted by the tissue traction device 100. As illustrated in FIG. 2, to increase traction on the target tissue TA, an additional traction section 120 is extended to additional traction tissue TR2 spaced apart from the traction tissue TR1 to which the traction-tissue-engaging segment 114 is engaged (as illustrated in FIG. 2), or to the same target tissue TT1 to which the traction-tissue-engaging segment 114 is engaged (such as illustrated in FIG. 4, FIG. 5, FIG. 6, and FIG. 7, as discussed in further detail below). The additional traction section 120 may be engaged with additional traction tissue TT1, TT2 along a traction-tissue-engaging segment 124 along the additional traction section 120. Although such traction-tissue-engaging segment 124 is illustrated in FIG. 3 as along a traction-tissue-engaging end 103 of the tissue traction device 100, a traction-tissue-engaging segment 124 of the additional traction section 120 may be located at other positions along the additional traction section 120. It will be appreciated that the tissue-manipulating device 400 or another device (e.g., an end effector, a hook, a grasper, etc.) may be used to engage the additional traction sections 120, 130 of the tissue traction device 100 with traction tissue.

In the example of an embodiment of a tissue traction device 100 illustrated in FIG. 3, the additional traction sections 120, 130 are in the form of loops positioned one within the other and coupled to/extending from the target-tissue-engaging segment 112 of the peripheral section 110 of the tissue traction device 100. The additional traction sections 120, 130 may be coupled with the peripheral section 110 along the target-tissue-engaging segment 112 thereof, such as to direct traction to the target tissue, to optimize the distance the additional traction section extends from the target tissue to the target tissue, to create a generally straight force vector being applied between the traction tissue the target tissue, to vary the force vectors (e.g., magnitude and/or direction), etc. A tissue traction device 100 formed in accordance with various principles of the present disclosure may have additional interior traction sections within the illustrated additional traction sections 120, 130, the present disclosure not being limited to a particular number of additional traction sections. Each additional traction section may be engaged (directly or indirectly) with further traction tissue which may be increasingly spaced apart from the traction tissue with which a traction section of the tissue traction device 100 has already been engaged, or to generally the same traction tissue site, such as to apply greater traction to the target tissue and/or to adjust the angle of the traction applied to the target tissue.

It will be appreciated that a tissue traction device formed in accordance with various principles of the present disclosure allows a medical professional to vary the force vector of traction applied to target tissue by engaging one or more segments of the tissue traction device with traction tissue (at the same site, or spaced apart sites) to facilitate performance of any of a variety of procedures on or around the target tissue. For instance, as target tissue is resected or dissected or otherwise moved with respect to surrounding tissue at the target tissue site, traction applied by the tissue traction device may be reduced. To maintain a constant amount of traction on the target tissue, instead of moving the initial traction-tissue-engaging segment of the tissue traction device (as in prior art procedures), one or more additional traction-tissue-engaging segments of the tissue traction device may be engaged (simultaneously and/or sequentially) with traction tissue. Although the traction tissue sites may be spaced increasingly apart from one another, such as illustrated in FIG. 1 and FIG. 2, the additional traction sections 120, 130 (etc.) of a tissue traction device 100 formed in accordance with various principles of the present disclosure may, instead, all be engaged with traction tissue in generally the same tissue area, such as in the example of use illustrated in FIG. 4, FIG. 5, FIG. 6, and FIG. 7.

It will be appreciated that engaging more than one segment or section of a tissue traction device to tissue at generally the same region or area or point may present various challenges. For instance, if different tissue-engagement members are used, generally a limited number of tissue-engagement members may be engaged with tissue at a particular tissue site. If the same tissue-engagement member is used to engage one or more segments or sections of a tissue traction device with tissue, there is a risk of one or more of the segments of sections of the tissue traction device inadvertently disengaging from the tissue-engagement member. For instance, a tissue-engagement member in the form of a clip with grasper arms shiftable between open and closed configurations may lose grasp of a segment or section of a tissue traction device while attempting to engage or maintain engagement with another segment or section of the tissue traction device.

Figure 4:
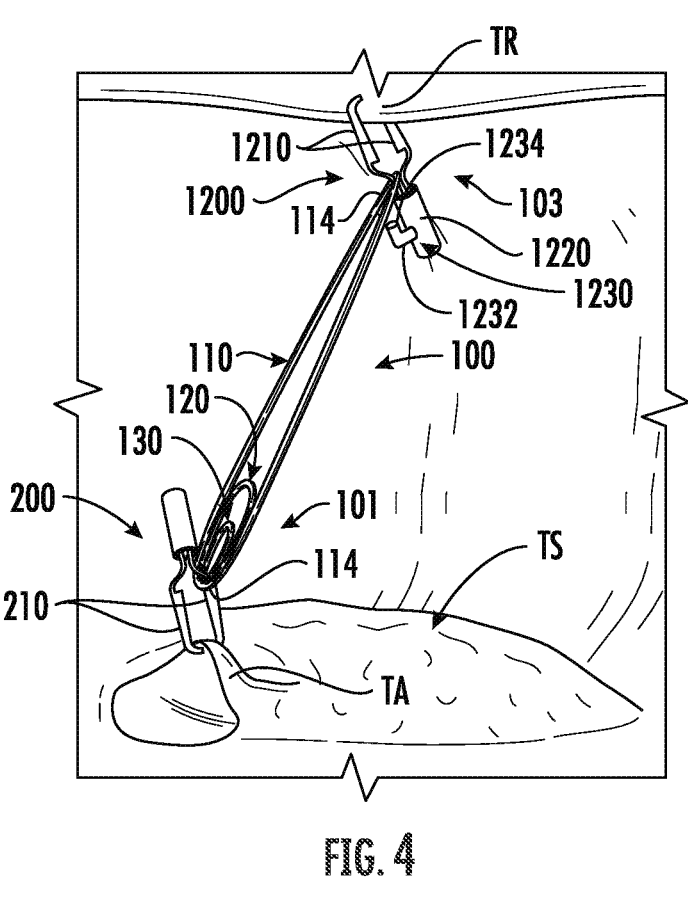
FIG. 4 illustrates an example of an environment in which an example of an embodiment of a traction device and system is being implemented, similar to that of FIG. 1, but with a modified tissue-engagement member.
Figure 5:
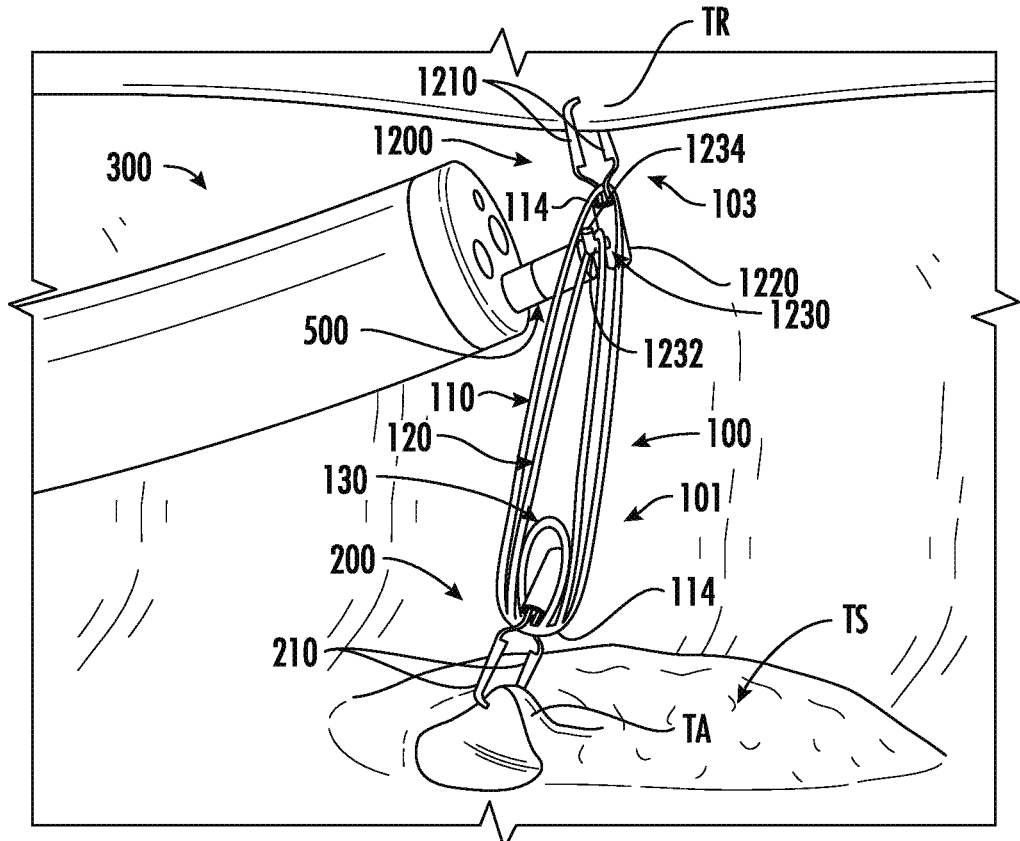
FIG. 5 illustrates an example of an environment and tissue traction device and system as in FIG. 4, with further traction being applied.
Figures 6, 7:
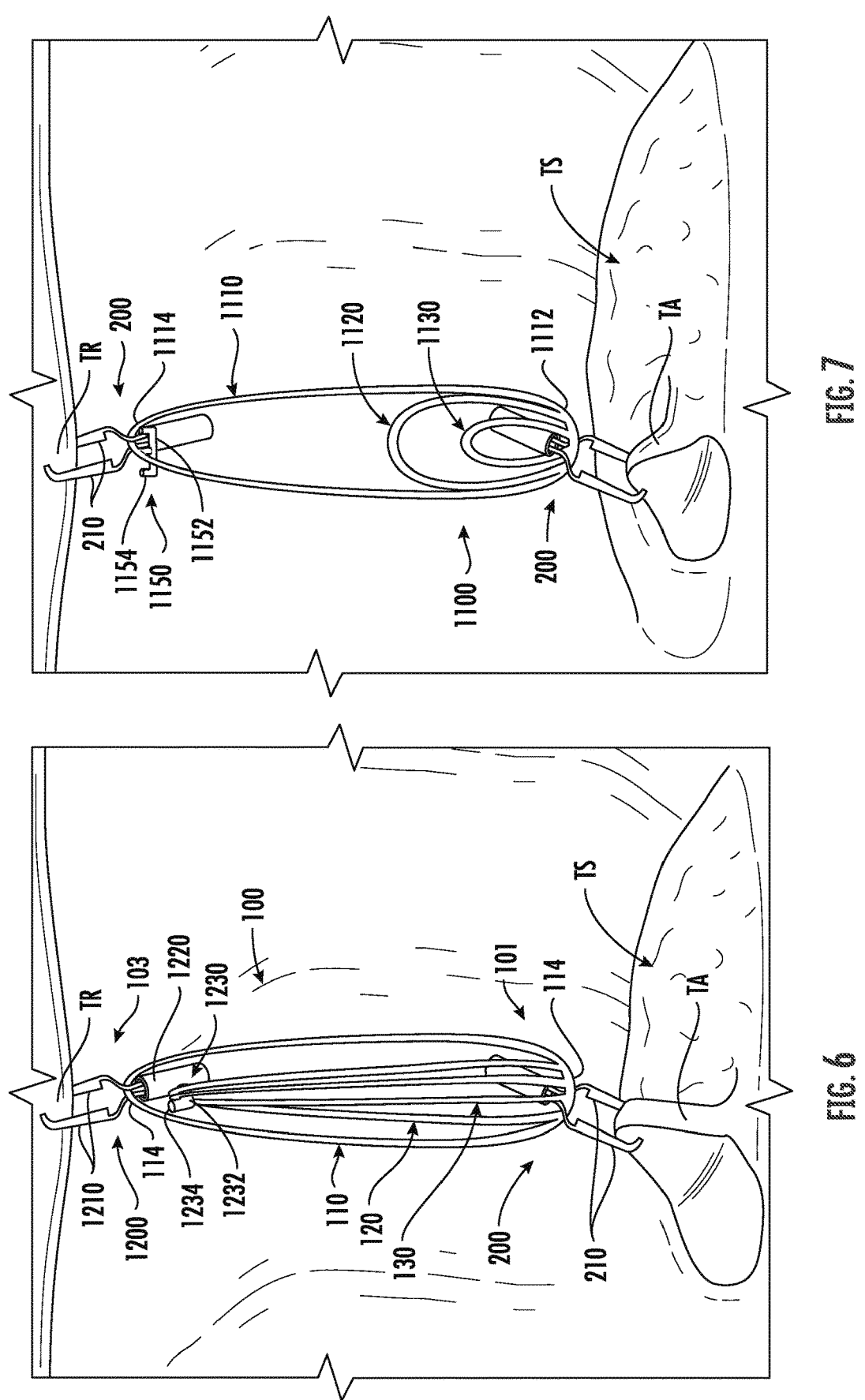
FIG. 6 illustrates an example of an environment and tissue traction device and system as in FIG. 4 and FIG. 5, with further traction being applied.
FIG. 7 illustrates an example of an environment in which an example of an embodiment of a traction device and system is being implemented, similar to that of FIG. 1 and FIG. 4, but with a modified tissue traction device.

To facilitate engagement of more than one traction-tissue-engaging segment or section of a tissue traction device with a common traction tissue site (at generally the same location, generally spaced apart from target tissue with which the tissue traction device is initially engaged), a modified tissue-engagement member may be used for all of the traction-tissue-engaging segments or sections to be engaged with the common traction tissue site. An example of an embodiment of a modified tissue-engagement member 1200 formed in accordance with various principles of the present disclosure is illustrated in FIG. 4, FIG. 5, and FIG. 6. In accordance with various principles of the present disclosure, a modified tissue-engagement member 1200 is configured for engagement with more than one segment or section of a tissue traction device 100 (such as formed in accordance with various principles of the present disclosure, or another tissue traction device) such as by engaging at least one segment or section of the tissue traction device 100 with the grasper arms 1210 of the tissue-engagement member 1200 and one or more other segments or section of the tissue-engagement member 1200 with another structure of the tissue-engagement member 1200. For instance, in the example of an embodiment illustrated in FIG. 4, FIG. 5, and FIG. 6, a modified tissue-engagement member 1200 has a modified capsule 1220 configured to engage one or more other segments or sections of the tissue-engagement member 1200 therewith. The modified capsule 1220 may include a hanger 1230 integrally formed with or separately formed and coupled with the capsule 1220. The hanger 1230 is sized, shaped, configured, and/or dimensioned to be engaged with one or more segments or sections of a tissue traction device, as well as to retain such segments or sections in engagement with the tissue-engagement member 1200. For instance, the hanger 1230 may include an arm 1232 extending away from (e.g., generally transverse to the wall of) the capsule 1220, and a hook 1234 extending transverse to the arm 1232, such as may be appreciated with reference to FIG. 4. The arm 1232 and the hook 1234 may be dimensioned to retain more than one section or segment of a tissue traction device 100 in engagement with the hanger 1230 and with respect to the tissue-engagement member 1200. The hook 1234 may be sized, shaped, configured, and/or dimensioned, such as with respect to the arm 1232, to retain more than one section or segment of a tissue traction device 100 in engagement with the arm 1232. It will be appreciated that other configurations of hangers than the illustrated hanger 1230 are within the scope and spirit of the present disclosure.

As illustrated in FIG. 4, a target-tissue-engaging segment 112 of a tissue traction device 100 such as described above may be engaged with target tissue TA (optionally with the use of a tissue-engagement member 200 such as described above) and a traction-tissue-engaging segment 114 of the tissue traction device 100 may be engaged with traction tissue TR with a modified tissue-engagement member 1200 such as described above. As the target tissue TA is manipulated or moved with respect to surrounding tissue in the target tissue area TA and traction on the target tissue TA is reduced, a device 500 (such as an end effector, hook, grasper, etc., or the tissue-manipulating device 400 used on the target tissue TA, as illustrated in FIG. 1 or FIG. 2) may engage another section or segment of the tissue traction device 100 with the modified tissue-engagement member 1200, such as by hooking one or more of the additional traction sections 120, 130 of the tissue traction device 100 on the hanger 1230. In the example illustrated in FIG. 5, the additional traction section 120 is engaged with the hanger 1230. It will be appreciated, however, that a different additional traction section, such as a smaller additional traction section 130, may be engaged with the hanger 1230 before or after or instead of the illustrated additional traction section 120. For instance, as illustrated in FIG. 6, more than one additional traction sections 120, 130 may be engaged with the hanger 1230.

Instead of engaging additional sections or segments of a tissue traction device to the same tissue-engagement member to engage such additional sections or segments to generally the same traction tissue TR, the additional sections or segments may be engaged with structure on a modified tissue traction device 1100, such as illustrated in FIG. 7. More particularly, the example of an embodiment of a modified tissue-engagement member 1200 illustrated in FIG. 7 includes a hanger 1150 integrally formed with or separately formed and coupled with the peripheral section 1110 of the modified tissue traction device 1100. The hanger 1150 is sized, shaped, configured, and/or dimensioned for engagement of more than one segment or section of the modified tissue traction device 1110 therewith, as well as to retain such segments or sections in engagement with the hanger 1150. For instance, the hanger 1150 may include one or more arms 1152 with one or more hooks 1154 extending transverse to the arms 1152. The arm 1152 and the hook 1154 may be dimensioned to retain more than one section or segment of the modified tissue traction device 1100 in engagement with the hanger 1150. The hook 1154 may be sized, shaped, configured, and/or dimensioned, such as with respect to the arm 1152, to retain more than one section or segment of the modified tissue traction device 1100 in engagement with the arm 1152. It will be appreciated that other configurations of hangers than the illustrated hanger 1150 are within the scope and spirit of the present disclosure.

It will be appreciated that various modifications to a tissue traction device 100, 1100 formed in accordance with various principles of the present disclosure may be made without departing from the scope and spirit of the present disclosure, For instance, the thickness of one or more sections of a tissue traction device 110, 1110 formed in accordance with various principles of the present disclosure need not be the same. For instance, thicker areas or regions of an additional traction section 120, 130 may be provided such as to increase resistance to elongation of such section, such as to increase traction applied by such section. Alternatively or additionally, at least one traction section may be formed of a different material (e.g., similar material composition but with differ- ent properties such as different moduli of elasticity and/or durometers, different material compositions such as different elastomers, etc.). Alternatively or additionally, the different traction sections need not all be coplanar. Alternatively or additionally, additional traction sections may be provided within the illustrated traction sections, and/or along other locations on the tissue traction device. Alternatively or additionally, although the illustrated additional traction sec- tions are illustrated one within the other, other configura- tions are within the scope and spirit of the present disclosure. Alternatively or additionally, although the illustrated addi- tional traction sections are illustrated one within the other and internally tangent to one another, other configurations are within the scope and spirit of the present disclosure. Alternatively or additionally, although the illustrated addi- tional traction sections are illustrated one within the other and internally tangent to the interior of the peripheral section, other configurations are within the scope and spirit of the present disclosure. Alternatively or additionally, although the shapes of the illustrated additional tractions sections are generally similar, other configurations are within the scope and spirit of the present disclosure. Alter- natively or additionally, other configurations of the periph- eral section and/or the additional traction sections are within the scope and spirit of the present disclosure.

As described above, a segment of a tissue traction device formed in accordance with various principles of the present disclosure may be engaged with an initial tissue site (refer- enced as target tissue for the sake of simplicity and without intent to limit), such as with a tissue-engagement member (optionally pre-loaded on the tissue traction device), and then another segment of the tissue traction device may be engaged with another region of tissue (referenced herein as traction tissue and/or a traction tissue site for the sake of convenience and without intent to limit) to apply traction to the target tissue via the tissue traction device. The target tissue site may be within a body passage or lumen (such as, without limitation, a gastrointestinal tract such as the small or large intestine), with the traction tissue along a wall of the body passage or lumen opposite the target tissue. Of course, it will be appreciated that devices, systems, and methods in in accordance with various principles of the present disclo- sure may be used in connection with other anatomical regions and/or structures. Although embodiments of the present disclosure may be described with specific reference to medical devices and systems and procedures for treating the gastrointestinal system, it should be appreciated that such medical devices and methods may be used to treat tissues of the abdominal cavity, digestive system, urinary tract, reproductive tract, respiratory system, cardiovascular system, circulatory system, and the like.

All apparatuses and methods discussed herein are examples of apparatuses and/or methods implemented in accordance with one or more principles of this disclosure. These examples are not the only way to implement these principles but are merely examples, not intended as limiting the broader aspects of the present disclosure. Thus, references to elements or structures or features in the drawings must be appreciated as references to examples of embodi- ments of the disclosure, and should not be understood as limiting the disclosure to the specific elements, structures, or features illustrated. Other examples of manners of imple- menting the disclosed principles will occur to a person of ordinary skill in the art upon reading this disclosure. Although embodiments of the present disclosure may be described with specific reference to medical devices and systems and procedures for treating the gastrointestinal system, it should be appreciated that such medical devices and methods may be used to treat tissues of the abdominal cavity, digestive system, urinary tract, reproductive tract, respiratory system, cardiovascular system, circulatory sys- tem, and the like.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without depart- ing from the concept, spirit, or scope, or characteristics thereof. For example, various features of the disclosure are grouped together in one or more aspects, embodiments, or configurations for the purpose of streamlining the disclo- sure. However, it should be understood that various features of the certain aspects, embodiments, or configurations of the disclosure may be combined in alternate aspects, embodi- ments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently dis- closed embodiments are therefore to be considered in all respects as illustrative and not restrictive, the scope of the claimed subject matter being indicated by the appended claims, and not limited to the foregoing description or particular embodiments or arrangements described or illus- trated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A tissue traction system comprising:
   a tissue traction device having a peripheral section defining a perimeter, and a target-tissue-engaging segment engageable with target tissue;
   a first traction-tissue-engaging section within the perimeter of and coupled to said peripheral section; and
   a second traction-tissue-engaging section within said first traction-tissue-engaging section.

2. The tissue traction system of claim 1, wherein said first traction-tissue-engaging section is spaced apart from said target tissue-engaging segment.

3. The tissue traction system of claim 1, wherein said target-tissue-engaging segment is defined along said peripheral section.

4. The tissue traction system of claim 1, wherein said peripheral section and said first traction-tissue-engaging section are each in the form of a loop.

5. The tissue traction system of claim 4, wherein:
   said target-tissue-engaging segment is defined along said peripheral section; and said first traction-tissue-engaging section is internally tangent with said peripheral section adjacent said target-tissue-engaging segment.

6. The tissue traction system of claim 5, wherein said second traction-tissue-engaging section is internally tangent with said peripheral section.

7. The tissue traction system of claim 4, wherein said second traction-tissue-engaging section is in the form of a loop.

8. The tissue traction system of claim 1, wherein said target-tissue-engaging segment is defined along said peripheral section.

9. The tissue traction system of claim 8, wherein said first traction-tissue-engaging section is extendable to be spaced apart from said target-tissue-engaging segment.

10. The tissue traction system of claim 1, further comprising a hanger configured to hold at least one of said traction-tissue-engaging sections adjacent traction tissue.

11. A tissue traction device comprising:
   a peripheral section defining a perimeter of said tissue traction device;
   a first traction-tissue-engaging section extending within the perimeter of and coupled to said peripheral section; and
   a second traction-tissue-engaging section within said first traction-tissue-engaging section.

12. The tissue traction device of claim 11, wherein:
   said peripheral section defines a target-tissue-engaging segment engageable with target tissue; and
   said first traction-tissue-engaging section defines at least one traction-tissue-engaging segment spaced apart from said target-tissue-engaging segment and engageable with traction tissue.

13. The tissue traction device of claim 11, wherein:
   said peripheral section and said first traction-tissue-engaging section are each in the form of a loop; and
   said first traction-tissue-engaging section is internally tangent with said peripheral section.

14. The tissue traction device of claim 13, wherein said second traction-tissue-engaging section is in the form of a loop.

15. The tissue traction device of claim 11, wherein said first traction-tissue-engaging section is internally tangent with said peripheral section.

16. The tissue traction device of claim 15, wherein:
   said second traction-tissue-engaging section is internally tangent with said peripheral section; and
   at least one of said first traction-tissue engaging section or said second traction-tissue-engaging section is internally tangent with said peripheral section adjacent said target-tissue-engaging segment.

17. The tissue traction device of claim 11, wherein:
   said peripheral section defines a target-tissue-engaging segment engageable with target tissue and a traction-tissue-engaging segment spaced apart from said target-tissue-engaging segment and engageable with traction tissue; and
   said tissue traction device further comprises a hanger on said peripheral section adjacent said traction-tissue-engaging segment configured to hold a traction-tissue-engaging segment of said first traction-tissue-engaging section adjacent the traction tissue.

18. A tissue traction system comprising:
   a tissue-engagement member comprising:
      grasper arms engageable with tissue; and a hanger spaced apart from said grasper arms and configured to hold at least one traction-tissue-engaging segment of a tissue traction device adjacent the tissue; and a tissue-traction device comprising:

a peripheral section defining a perimeter;

a first traction-tissue engaging section extending within the perimeter; and a second-traction tissue-engaging section within said first traction tissue-engaging section.

19. The tissue-engagement member of claim 18, further comprising a capsule extending about said grasper arms, wherein said grasper arms are retractable into said capsule to shift into a closed configuration holding tissue therebetween, and said hanger extends from said capsule.

20. The tissue-engagement member of claim 18, wherein said grasper arms are further engageable with another traction-tissue-engaging segment of the tissue traction device to engage the other traction-tissue-engaging segment of the tissue traction device with tissue.

* * * * *